Figure 1:
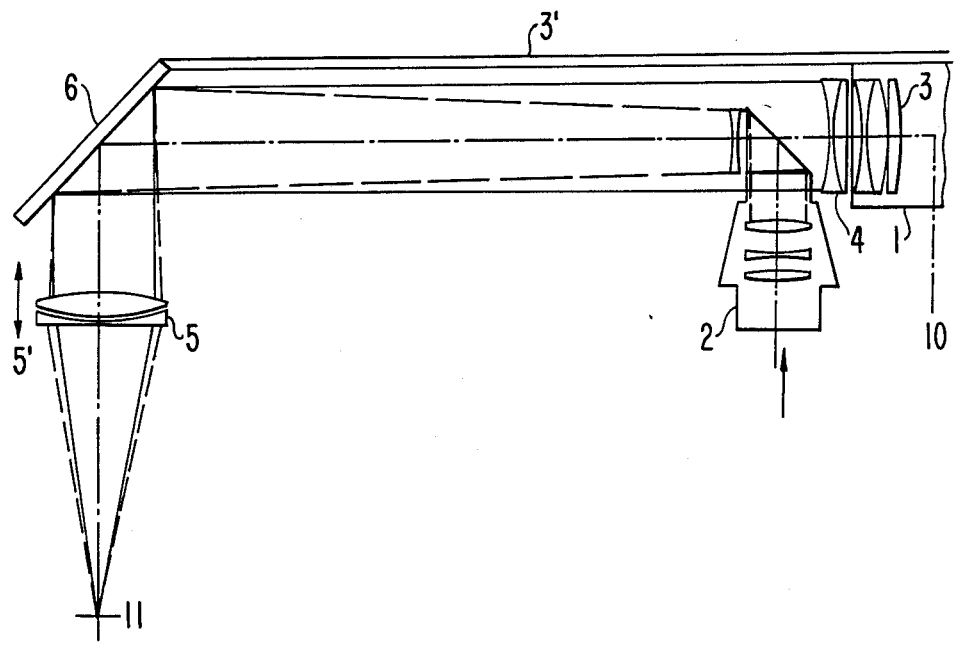

United States Patent [19]

Reis

[11] Patent Number: 4,865,441

[45] Date of Patent: Sep. 12, 1989

[54] APPARATUS USING A LASER FOR TREATING THE EYE

[75] Inventor: Werner Reis, Munich, Fed. Rep. of Germany

[73] Assignee: G. Rodenstock Instruments GmbH, Munich, Fed. Rep. of Germany

[21] Appl. No.: 222,726

[22] Filed: Jul. 22, 1988

[30] Foreign Application Priority Data

Jul. 22, 1987 [DE] Fed. Rep. of Germany ....... 3724283

[51] Int. Cl.$^4$ .......................... A61B 3/10; A61B 17/36
[52] U.S. Cl. ..................................... 351/214; 351/221; 128/303.1
[58] Field of Search ............... 351/205, 211, 214, 221; 128/303.1; 350/506, 618

[56] References Cited

U.S. PATENT DOCUMENTS

| | | |
|---|---|---|
| 3,703,176 | 11/1972 | Vassiliadis ............................ 351/221 |
| 4,477,159 | 10/1984 | Mizuno et al. ....................... 351/214 |
| 4,638,801 | 1/1987 | Daly et al. ......................... 128/303.1 |

*Primary Examiner*—Rodney B. Bovernick
*Assistant Examiner*—P. M. Dzierzynski
*Attorney, Agent, or Firm*—Antonelli, Terry & Wands

[57] ABSTRACT

An apparatus utilizing a laser for treating the eye of a patient in either a seated or supine position. The apparatus includes a slit lamp device having integrated laser beam guidance for examination and treatment of seated patients and a support element attachable to the casing of the microscope of the slit lamp device and carrying lens groups for and a deflection device for modifying the beam path and which enable bending of the laser beam, illumination beam and the observation beam path to the eye to be treated when the patient is in a supine position.

12 Claims, 1 Drawing Sheet

APPARATUS USING A LASER FOR TREATING THE EYE

The present invention relates to an apparatus using a laser for treating the eye of a patient.

Apparatuses of this type, in which the laser beam is guided by means of mirrors in a state-of-the art lamp device are known, by way of illustration, from DE-PS No. 33 31 431, DE-GM No. 86 01 287 or U.S. Pat. No. 4 638 801.

With these apparatuses using a laser for treating the eye, the person to be treated has to be in a seated position. In order to be able to carry out precise laser treatment, the person's head has to be held in a specific position. When the treatment takes long, it is unavoidable that there are signs of fatigue, making continued treatment difficult or even impossible.

For this reason, it has already been proposed to lay the persons to be treated on an operating table during the laser treatment, thereby contributing significantly to the patient's relaxing. Moreover, the contact lens positioning is ergonomically much more favorable for the examiner. Due to the supine position, it is easier to put the eye at rest permitting improved laser aim and hitting; this is particularly important in macula-close laser treatment.

In one known-in-the-art apparatus for using a laser to treat the eye of a patient lying on an operation table, a beam-directing device is provided for the laser, which directs the laser beam with a three-fold 90> deflection from a laser unit, which is positioned under the operating table, to the location to be treated. A beam-directing device of this type—as is quite evident—is not suited for treating seated patients.

Therefore, it is necessary according to the state of the art to provide an apparatus for treatment for seated patients and an apparatus for supine patients when a patient is to be treated in a sitting or lying position depending on the case at hand.

The primary object of the present invention is to provide an apparatus using a laser for treating the eye, which permits treating a patient lying on an operation table as well as treating a seated one.

Remarkably, the primary object on which the present invention is based is solved by proceding from a slit lamp device known in the art with integrated laser-beam guidance and providing this slit lamp device with a support element to which the elements required for treatment of a supine patient are attached. As a result of these elements intersection length is extended, i.e. the adaption of the beam path to the altered "patient location" as well as the direction of the beam in the patient's eye.

The invented apparatus has the advantage that it can be quickly converted from treatment for supine patients to seated ones.

Furthermore, it is easy to operate for, due to the invented arrangement of the individual parts, all the operational elements continue to be within easy reach of the comfortably seated operator.

According to a feature of the present invention, the optical system for extending the intersection length may be provided with a negative and a positive lens group; whereby it is particularly advantageous if the positive lens group can be shifted for focussing the observation beam path and/or the laser beam and the illumination beam as this permits a simple and sure sharp focussing on the location to be treated.

The particularly advantageous further embodiment provides that the microscope objective is neutralized by the negative lens group resulting in a parallel beam path between the negative and the positive lens groups. By means of such a beam path, the intersection length for the observation and the illumination beam path can be extended or shortened to a limited degree without any substantial image alterations. In this manner—if the support element is designed as a telescopic rail—simple adaption to the given spatial circumstances etc. is possible.

According to another feature of the present invention, the extension of the intersection length is achieved by the fact that the lens group facing the patient of the microscope objective of the split lamp can be removed and attached to the support element. In this case, of course, a prerequisite is a parallel beam path, so that again an intersection length extension or shortening can be realized without any substantial image alterations.

Naturally, the same optical elements can be employed for the observation beam path, the illumination beam path and the laser beam.

In particular with slit lamp devices, in which the light beam of the slit lamp encloses an angle in a vertical plane to the observation beam path, it is, however, advantageous if, an additional lens group can be attached to the slit lamp for the extension of the intersection length of the illumination light. Depending on the geometry of the beam path of the slit lamp, it may also be necessary to separate one or even all the optical elements of the beam path of the slit lamp from those of the observation beam path.

The fundamental feature of creating an apparatus using a laser for treating the eye with the option of being suitable for treating seated or supine patients based on an apparatus known in the art intended for seated patients can be used on the most varied slit lamp devices.

Furthermore, the realization of the fundamental feature is to a large extent independent of the design of the laser beam guidance in the slit lamp device.

By way of illustration, the laser beam can be guided through the arm of the microscope—as known, by way of illustration, from DE-PS No. 33 31 431—or through the slit lamp, as proposed in DE-GM No. 86 01 287.

It is also possible to guide the laser beam in the beam path with mirrors independently of the design of the microscope encasement or the design of the lamp by means of a prism or the like arranged externally. An apparatus of this type is, by way of illustration, known from U.S. Pat. No. 4 638 801.

Figure 2:
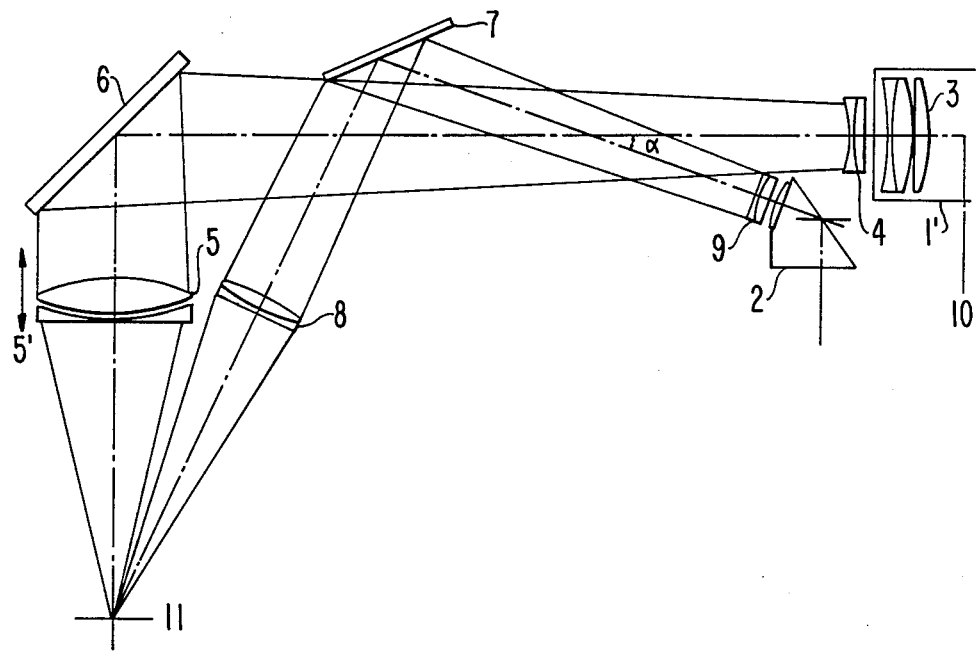

The present invention is made more apparent hereafter using preferred embodiments with reference to the drawing, depicting:

FIG. 1 a first preferred embodiment, in which the observation and the illumination beam path are guided via a deflection device, and FIG. 2 a second preferred embodiment, having separate deflection devices for the observation and the illumination beam path.

FIG. 1 shows a first preferred embodiment of apparatus provided with a microscope 1 serving as the observation device and a slit lamp 2 employed as the illumination device.

The microscope 1 is provided with a microscope objective 3, the intersection length of which is designed for the working distance in treating a seated patient. In accordance with the present invention, attached to the encasement of microscope 3 is a removable support element 3', on which are mounted a negative lens group 4 and a positive lens group 5 for extending the intersection lengths and a deflection element 6, by way of illustration a mirror or a prism.

The focal distance of lens group 4 in the depicted preferred embodiment is inversely equal to the focal distance of microscope objective 3 and is, by way of illustration, −130 mm. As a result there is a parallel beam path between the negative and the positive lens groups so that the intersection length for the observation and illumination beam path may be extended or shortened to a limited degree without any substantial image alterations and may be used if a telescopic rail is employed to adapt the apparatus to special work conditions.

Lens group 5 is arranged in a shitable manner in the direction of arrow 5' in such a fashion that focussing the beam path on the eye 11 to be treated is possible. The focal distance of lens group 5 in the shown preferred embodiment is equal to the focal point of the microscope objective 3 and is, by way of illustration, 130 mm.

Beam 10 of a laser, which is not depicted, is guided in the microscope encasement in a state of the manner in such a fashion that the laser beam also passes elements 4 to 6.

FIG. 2 shows a further preferred embodiment, in which corresponding elements like FIG. 1 are provided with the same designations although the removable support element 3 of FIG. 1 is not illustrated. The difference between the two preferred embodiments is that in FIG. 2 beam path 2' of slit lamp 2 encloses in a vertical plane an angle 2 with the observation beam path.

For this reason, separate deflection devices 6 and 7 have been provided for the two beam paths. Furthermore, a separate negative lens group 9 has been provided for the illumination beam path and a positive lens group 8 for extending the intersection length and for focussing the illumination light.

Beam 10 is guided by means of mirrors in illumination device 1—like in the preferred embodiment illustrated in FIG. 1.

The relative compact construction of the apparatus permits manifold use. Therefore, the apparatus can be employed for the examination and treatment of supienras well as seated patients. The beam path can be determined at any time with the aid of the mirror deflection device.

At any rate, the apparatus has a number of advantages:

The removable support element for extending the intersection length of the microscope-laser-illumination-focus makes it possible to quickly convert a slit lamp for treating a seated patient or a supine one. Despite its convertability, contrary to the state of the art operating microscopes, the result is a sturdy construction. Moreover, the transferal of the entire slit lamp system and all the accessories, such as video devices, etc., is possible. The working distance is measured in such a manner that not only good focussing on the eye to be treated is yielded, but also that the eye is accessable to the hands of the examiner so that he/she can easily apply a contact lens, etc.

The apparatus is suited, of course not only for laser treatment, but also for examining and as a substitute for conventional operating microscopes.

It is particularly advantageous that due to the support element provided in accordance with the present invention, full mobility of the split lamp device, such as independent rotatability of the slit lamp and the microscope, height adjustability, etc., continues to be retained.

In the preceding, the present invention was described using preferred embodiments without the intention of limiting or restricting the overall scope of concept of the present invention within the scope of which the most varied modifications are possible: By way of illustration, instead of a rigid support element, a telescopic arm can be employed, which permits adaption to the spatial circumstances, etc. The attachment of the elements to the telescopic arm or support element and to the slit lamp can occur by the most varied means, by way of illustration, by means of magnetic holders, but also rigid, etc.

Furthermore, various flat plates, if required with weak meniscus lenses, may be used to balance the illumination.

Of course, the laser beam may also be guided by means of mirrors in a different manner than is described in the preferred embodiments in connection with FIGS. 1 and 2: by way of illustration, the laser beam may be guided through the slit lamp, through a separate pivot or through a prism additionally provided in the beam path of the apparatus.

It is also possible to provide a separate support element for the deflection element, which deflects the beam path of the illumination light.

What I claim is:

1. An apparatus for using a laser to treat the eye of a patient in one of a seated or supine position, comprising: a slit lamp device for examination and treatment of a seated patient, microscope for observation, an illumination system, means for coupling laser light to the slit lamp device for enabling treatment of the eye of the patient, and position treatment means for enabling treatment of the patient with the laser light when the patient is in one of a seated and supine position, the position treating means including support means for detachable attachment to the microscope, and an optical system for modifying a beam path of the slit lamp device including a beam deflection element, the optical system and beam deflection element being coupled to the supporting means so as to enable the beam path of the slit lamp device facing the patient to be elongated in a horizontal direction and deflected downwardly to the eye of the patient when the patient is in a supine position.

2. An apparatus according to claim 1, wherein the optical system for modifying the beam path includes a negative lens group and a positive lens group.

3. An apparatus according to claim 2, wherein the positive group is mounted so as to enable movement thereof for focusing at least one of the illumination beam and the laser beam.

4. An apparatus according to claim 2, wherein the negative lens group enable neutralization of an object of the microscope.

5. An apparatus according to claim 1, wherein the optical system for modifying the beam path includes a lens group which is a lens group initially forming a lens group of a microscope objective facing and which is detached from and coupled to the supporting means.

6. An apparatus according to claim 1, wherein the supporting means comprises a telescopic member.

7. An apparatus according to claim 1, further comprising an additional lens group coupled to the slit lamp device for modifying a beam path of an illumination light.

8. An apparatus according to claim 1, further comprising a separate deflection device for a light beam from the slit lamp device.

9. An apparatus according to claim 1, further comprising a separate lens group is provided for a light beam from the slit lamp device.

10. A apparatus according to claim 1, wherein the microscope enables guiding of a light beam through an arm of the microscope.

11. An apparatus according to claim 1, wherein the slit lamp device enables the guiding of the laser beam therethrough.

12. An apparatus according to claim 1, further comprising mirror means and a deflection element separate from the slit lamp device and microscope for guiding the laser beam.

* * * * *